US00PP35184P2

(12) United States Plant Patent
Koppe

(10) Patent No.: US PP35,184 P2
(45) Date of Patent: May 23, 2023

(54) ***BEGONIA* PLANT NAMED 'KRHAISU01'**

(50) Latin Name: ***Begonia* x *hiemalis***
Varietal Denomination: KRHAISU01

(71) Applicant: KOPPE ROYALTY B.V., Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 17/844,021

(22) Filed: Jun. 19, 2022

(51) Int. Cl.
*A01H 5/02* (2018.01)
*A01H 6/18* (2018.01)

(52) U.S. Cl.
USPC ..... Plt./344

(58) Field of Classification Search
USPC ..... Plt./343, 344
See application file for complete search history.

(56) References Cited

PUBLICATIONS http://flora-land.ro/floraland/wp-content/uploads/2021/07/Koppe-catalogus-2021-2022. Retrieved from the Internet on Aug. 25, 2022 (2 pages total).*

* cited by examiner

*Primary Examiner* — Susan McCormick Ewoldt
(74) *Attorney, Agent, or Firm* — C. Anne Whealy

(57) ABSTRACT

A new and distinct cultivar of *Begonia* plant named 'KRHAISU01' characterized by its broadly upright to spreading and mounded plant habit; moderately vigorous growth habit and moderate growth rate; moderately freely branching habit; dark green-colored leaves; freely flowering habit; double-type male flowers that are pinkish apricot in color and held above and beyond the foliar plane; and good postproduction longevity.

2 Drawing Sheets

Figure 1:
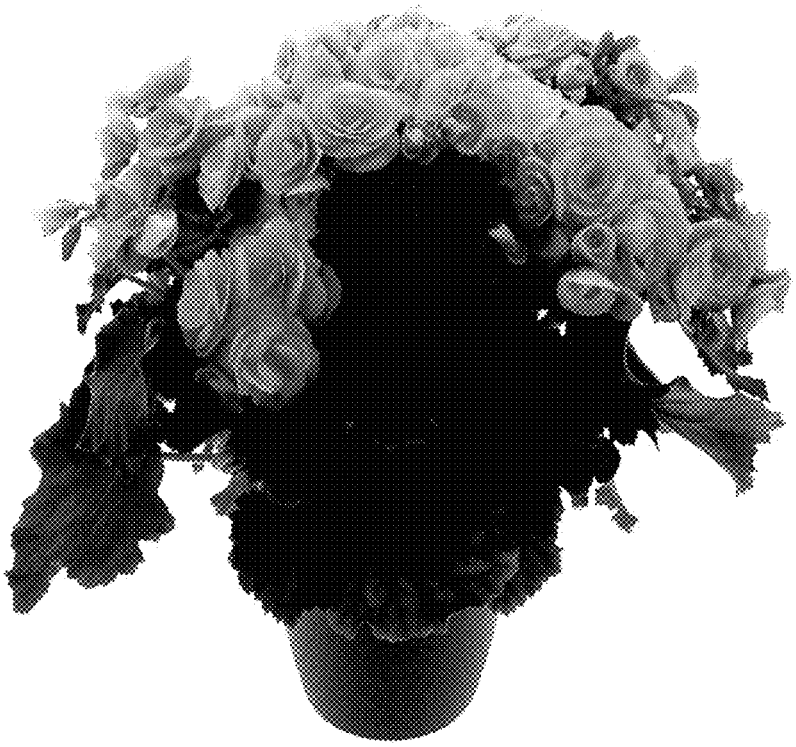

Botanical designation: *Begonia* x *hiemalis*.
Cultivar denomination: 'KRHAISU01'.

STATEMENT REGARDING PRIOR DISCLOSURES BY THE INVENTOR/APPLICANT & ASSIGNEE

An European Community Plant Breeder's Rights application for the instant plant was filed by the Applicant/Assignee, Koppe Royalty B.V. of Putten, The Netherlands on Nov. 23, 2021, application number 2021/3016. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRHAISU01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant originated from a cross-pollination made by the Inventor in March, 2014 of a proprietary selection of *Begonia* x *tuberhybrida* identified as code number KV14-3481-004, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in May, 2015.

Asexual reproduction of the new *Begonia* plant by terminal vegetative cuttings taken in a controlled greenhouse environment in Ermelo, The Netherlands since August, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRHAISU01'. These characteristics in combination distinguish 'KRHAISU01' as a new and distinct *Begonia* plant:

1. Broadly upright to spreading and mounded plant habit.
2. Moderately vigorous growth habit and moderate growth rate.
3. Moderately freely branching habit.
4. Dark green-colored leaves.
5. Freely flowering habit.
6. Double-type male flowers that are pinkish apricot in color and held above and beyond the foliar plane.
7. Good postproduction longevity.

Plants of the new *Begonia* differ primarily from plants of the female parent selection in flower color as plants of the new *Begonia* have pinkish apricot-colored flowers whereas plants of the female parent selection have salmon orange-colored flowers.

Plants of the new *Begonia* differ primarily from plants of the male parent selection in the following characteristics:

1. Plants of the new *Begonia* have double flowers whereas plants of the male parent selection have single flowers.
2. Plants of the new *Begonia* have pinkish apricot-colored flowers whereas plants of the male parent selection have purplish pink-colored flowers.

Plants of the new *Begonia* can be compared to plants of *Begonia* x *hiemalis* 'Dark Netja', not patented. In side-by-side comparisons conducted in Ermelo, The Netherlands, plants of the new *Begonia* differ primarily from plants of 'Dark Netja' in flower color as flowers of plants of the new *Begonia* are pinkish apricot in color whereas flowers of plants of 'Dark Netja' are bright pink in color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical plant of 'KRHAISU01' grown in a container.

Figure 2:
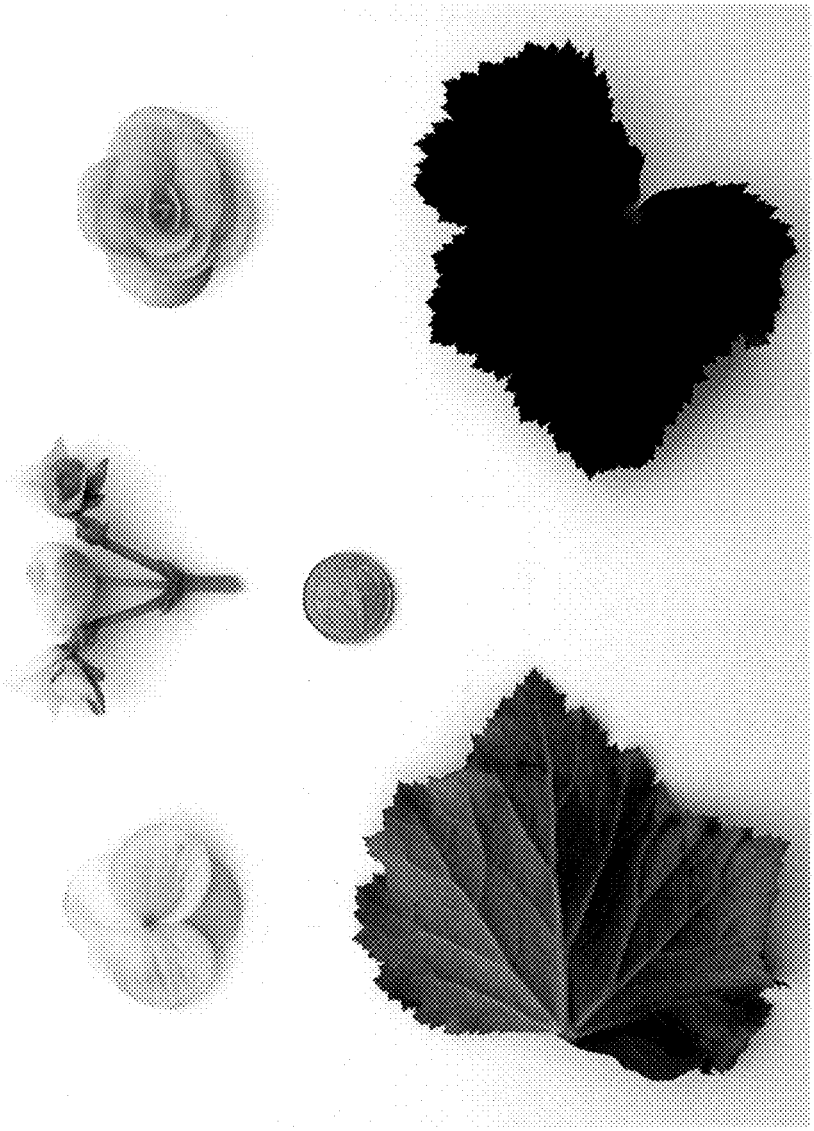

The photograph on the second sheet (FIG. 2) are close up views of the upper (right) and lower (left) surfaces of typical leaves and flowers of 'KRHAISU01', and in the center of the photograph is a close-up view of typical flower buds.

DETAILED BOTANICAL DESCRIPTION

The aforementioned photographs and following observations and measurements describe plants grown during the autumn in 13-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRHAISU01'.

Parentage:

*Female, or seed, parent*.—Proprietary selection of *Begonia* x *tuberhybrida* identified as code number KV14-3481-004, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orangish brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Broadly upright to spreading and mounded plant habit; overall plant shape, roughly globular.

*Growth habit*.—Moderately vigorous growth habit and moderate growth rate; suitable for 9-cm and larger containers; under optimal environmental and cultural conditions, usually about eleven weeks from rooted cuttings are required to produce proportional plants in 13-cm containers.

*Branching habit*.—Moderately freely branching with about five primary branches each with about two secondary branches developing per plant.

*Plant height, soil level to top of foliar plane*.—About 25.6 cm.

*Plant height, soil level to top of floral plane*.—About 28.8 cm.

*Plant width*.—About 42.1 cm.

*Lateral branches*.—Length: About 11.8 cm. Diameter: About 8 mm. Internode length: About 3.2 cm. Strength: Moderately strong. Aspect: Erect to about 50° from vertical. Texture and luster: Sparsely pubescent; slightly glossy. Color, developing: Close to 146C to 146D. Color, developed: Close to 146A. Lenticels: None observed on plants of the new *Begonia* to date.

*Leaves*.—Arrangement: Alternate, simple. Length: About 14.1 cm. Width: About 12.6 cm. Shape: Broadly ovate, unequal. Apex: Acute to minutely apiculate. Base: Oblique, lobes free and not imbricate. Margin: Serrate to dentate; slightly to moderately undulate. Texture and luster, upper surface: Smooth, glabrous; velvety; slightly glossy. Texture and luster, lower surface: Mostly smooth, glabrous with sparse pubescence along the veins; velvety; moderately glossy. Venation pattern: Pinnate. Color: Developing leaves, upper surface: Close to 137A. Developing leaves, lower surface: Close to a blend of 147B and 148B. Fully expanded leaves, upper surface: Darker than a blend of 147A and N189A; venation, close to 137A and 137B. Fully expanded leaves, lower surface: Close to 191A; venation, close to 146A to 146B. Petioles: Length: About 6.4 cm. Diameter: About 5.5 mm. Strength: Low, flexible. Texture and luster, upper and lower surfaces: Sparsely pubescent; slightly glossy. Color, upper surface: Close to a blend of 146A and 148A moderately tinged with close to 182B; distally, strongly tinged with close to 180A to 180B. Color, lower surface: Close to a blend of 146A and 148A. Stipules: Quantity and appearance: Two leafy stipules at the base of each leaf. Length: About 8.5 mm. Width: About 8.5 mm. Shape: Broadly ovate to roughly deltoid. Apex: Broadly acute. Base: Broadly cuneate. Margin: Ciliate. Color, upper and lower surfaces: Close to 145B; venation, close to 182B to 182C.

Flower description:

*Flower form and flowering habit*.—Fully double-type male rotate flowers arranged in axillary cymes; to date, female flower development has not been observed on plants of the new *Begonia*; typically about 13 flowers per cyme, numerous cymes in flower simultaneously and about 600 flowers developing per plant; flowers face upright to outwardly and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height*.—About 17.1 cm.

*Inflorescence diameter*.—About 11.7 cm.

*Flower buds*.—Length: About 1.8 cm. Diameter: Ranging from about 1 cm to 2.1 cm. Shape: Roughly circular to reniform, flattened. Texture and luster: Smooth, glabrous; slightly velvety; slightly glossy. Color: Close to 35C to 35D; towards the base, close to 151D.

*Male flowers*.—Diameter: About 4.9 cm by 5.7 cm. Depth: About 2.5 cm. Tepals: Quantity and arrangement: About four arranged in two whorls. Length, inner whorl tepals: About 2.7 cm. Length, outer whorl tepals: About 3.1 cm. Width, inner whorl tepals: About 3 cm. Width, outer whorl tepals: About 3.3 cm. Shape: Reniform to roughly orbicular. Apex: Mostly rounded. Base, inner whorl tepals: Cuneate. Base, outer whorl tepals: Truncate. Margin: Entire, not undulate. Texture and luster, upper surface: Smooth, glabrous; velvety; not rugose; matte. Texture and luster, lower surface: Smooth, glabrous; moderately velvety; not rugose; inner whorl tepals, matte and outer whorl tepals, slightly glossy. Color, inner whorl tepals: When opening, upper surface: Close to 18B; towards the margins and apex, close to 31C and 31D and towards the base, close to 1C. When opening, lower surface: Close to 18B and 19B; towards the margins and apex, close to 24C. Fully opened, upper surface: Close to 36B; towards the basal margins, close to 38A; at the base, close to 154C to 154D; venation, close to 147D; color does not change with subsequent development. Fully opened, lower surface: Close to 36B; towards the basal margins, close to 38A; at the base, close to 154C to 154D; venation, close to 147D; color does not change with subsequent development. Color, outer whorl tepals: When opening, upper surface: Close to 154D; towards the margins and apex, close to 35D. When opening, lower surface: Close to a blend of 150C and 154D; towards the margins and apex, close to 35C to 35D. Fully opened, upper surface: Close to 154D; towards the margins and apex, close to 37C and 37D; venation, close to 147D; color does not change with subsequent development. Fully opened, lower surface: Close to 145D; towards the margins and apex, close to 38A and 38B; venation, close to 147D; color does not change with subsequent development. Tepaloids: Quantity and arrangement per flower: Variable, about 17 per flower arranged in about four whorls. Length: About 1.5 cm to 2.6 cm. Width: About 1.4 cm to 2.7 cm. Shape: Obovate. Apex: Rounded. Base: Cuneate. Margin: Entire; not undulate. Texture and luster, upper surface: Smooth, glabrous; velvety; not rugose; matte. Texture and luster, lower surface: Smooth, glabrous; slightly velvety; not rugose; matte. Color: When opening, upper surface: Close to 14D; towards the margins, close to 24C. When opening, lower surface: Close to 13D; towards the margins, close to 24D. Fully opened, upper surface: Close to 36B; towards the basal margins, close to 38B and at the base, close to 154C to 154D; venation, similar to lamina color; color does not change with subsequent development. Fully opened, lower surface: Close to 37C to 37D and at the base, close to 154C to 154D; venation, close to 146D; color does not change with subsequent development.

*Flower bracts*.—Quantity and arrangement: Two positioned at the top of the peduncle. Length: About 1.7 cm. Width: About 1.6 cm. Shape: Broadly ovate to close to reniform. Apex: Broadly and bluntly acute. Base: Broadly cuneate. Margin: Ciliate. Texture and luster, upper and lower surfaces: Smooth, glabrous; moderately velvety; slightly glossy. Color, upper surface: Close to 144B; venation, close to 143A. Color, lower surface: Close to 144B; venation, close to 147B and distally slightly tinged with close to 182B.

*Peduncles*.—Length: About 7.6 cm. Diameter: About 5.5 mm. Strength: Moderately strong. Aspect: About 30° from lateral branch axis. Texture and luster: Smooth, glabrous; moderately glossy. Color: Close to 146A and 146B.

*Pedicels*.—Length: About 2.6 cm. Diameter: About 2 mm. Strength: Moderately strong. Aspect: About 30° from peduncle axis. Texture and luster: Smooth, glabrous; moderately glossy. Color: Close to 144A to 144B.

*Reproductive organs*.—To date, stamen and pistil development have not been observed on plants of the new *Begonia*.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KRHAISU01' as illustrated and described.

* * * * *